US006842642B2

(12) United States Patent
Vanhout

(10) Patent No.: US 6,842,642 B2
(45) Date of Patent: Jan. 11, 2005

(54) ADJUSTABLE CARDIAC RESYNCHRONIZATION

(75) Inventor: Warren L. Vanhout, Saline, MI (US)

(73) Assignee: Medtronic, Inc., Minneapolis, MN (US)

( * ) Notice: Subject to any disclaimer, the term of this patent is extended or adjusted under 35 U.S.C. 154(b) by 451 days.

(21) Appl. No.: 10/008,464

(22) Filed: Nov. 9, 2001

(65) Prior Publication Data

US 2003/0093122 A1 May 15, 2003

(51) Int. Cl.$^7$ ............................................. A61N 1/362
(52) U.S. Cl. ................................ 607/15; 607/9; 607/16
(58) Field of Search ........................... 607/4, 9, 15, 16

(56) References Cited

U.S. PATENT DOCUMENTS

| | | | |
|---|---|---|---|
| 4,562,841 A | | 1/1986 | Brockway et al. |
| 4,928,688 A | * | 5/1990 | Mower ........................... 607/9 |
| 5,085,656 A | | 2/1992 | Polaschegg |
| 5,487,752 A | | 1/1996 | Salo et al. |
| 5,540,727 A | * | 7/1996 | Tockman et al. ............. 607/18 |
| 5,697,884 A | | 12/1997 | Francischelli et al. |
| 5,792,193 A | | 8/1998 | Stoop |
| 5,807,234 A | | 9/1998 | Bui et al. |
| 6,048,328 A | | 4/2000 | Haller et al. |
| 6,070,101 A | * | 5/2000 | Struble et al. ................. 607/9 |
| 6,122,545 A | | 9/2000 | Struble et al. |
| 6,148,234 A | | 11/2000 | Struble |
| 6,223,079 B1 | | 4/2001 | Bakels et al. |
| 6,223,082 B1 | | 4/2001 | Bakels et al. |
| 6,256,536 B1 | | 7/2001 | Kramer |
| 6,292,693 B1 | | 9/2001 | Darvish et al. |
| 6,363,280 B1 | * | 3/2002 | Mouchawar et al. .......... 607/16 |

FOREIGN PATENT DOCUMENTS

WO    WO 97/25098    7/1997    ............ A61N/1/00

OTHER PUBLICATIONS

Higgins, S.L. et al., "Biventricular Pacing Diminishes the Need for Implantable Cardioverter Defibrillator Therapy," *J Am Coll of Cardiol*, vol. 3s6, No. 3, p. 824–7 (Sep. 2000).

* cited by examiner

*Primary Examiner*—Kennedy Schaetzle
(74) *Attorney, Agent, or Firm*—Paul H. McDowall; Girma Wolde-Michael

(57) ABSTRACT

Techniques are presented for providing adjustable cardiac resynchronization with an implanted medical device such as a pacemaker. For example, cardiac resynchronization may be provided during some time periods but not during other time periods, or cardiac resynchronization may be provided in response to selected sensed events. Adjustable cardiac resynchronization is applicable to therapy such as bi-ventricular pacing, in which both ventricles of the heart are paced in response to sensed atrial events.

16 Claims, 6 Drawing Sheets

ADJUSTABLE CARDIAC RESYNCHRONIZATION

TECHNICAL FIELD

The invention relates to cardiac pacing systems and, more particularly, to multiple-chamber cardiac pacing systems.

BACKGROUND

Many patients that suffer from congestive heart failure (CHF) develop a wide QRS complex resulting from a delayed activation of one of the ventricles in the heart. This ventricular "dysynchrony" may be caused by dilation of the heart, which disrupts the conduction pathways and interferes with depolarization sequences. Ventricular dysynchrony may worsen heart failure symptoms.

In a classic case of ventricular dysynchrony, the patient's right ventricle activates first, and the left ventricle activates at a later time. The patient often experiences a reduction in cardiac output because the ventricles begin contraction at slightly different times. The timing imbalance may also cause the patient to experience paradoxical septal motion, mitral regurgitation or decreased ventricular filling time.

Patients having a wide QRS complex may receive benefits from an implanted medical device, such as a pacemaker, that paces both ventricles. The implanted medical device senses atrial contractions, waits a predetermined time (or atrioventricular (AV) delay) after each sensed atrial contraction, and then paces both ventricles. The ventricles may be paced simultaneously, or one ventricle may be paced before another. This bi-ventricular pacing is one form of cardiac resynchronization, and it provides many CHF patients with improvements in quality of life, exercise capacity and overall cardiac function.

Generally speaking, cardiac resynchronization refers to pacing therapies applied by implanted medical devices with pacing leads in two or more chambers of the heart. In response to a sensed event, the pacemaker delivers pacing pulses to two chambers of the heart. The pacing pulses may be, but need not be, delivered simultaneously. Although the discussion that follows emphasizes bi-ventricular pacing to treat ventricular dysynchrony, cardiac resynchronization also encompasses, for example, resynchronization of atrial contractions.

Cardiac resynchronization, particularly bi-ventricular pacing, may increase the workload on the heart. A patient that responds to cardiac resynchronization typically experiences an increase in ejection fraction, i.e., the ratio of the blood ejected from a ventricle to the volume of the ventricle.

In addition, a patient that responds to cardiac resynchronization may suddenly experience cardiac failure at a later time. It is not known whether the cardiac failure is due to increased workload on the heart or to other factors. Although this phenomenon is subject to ongoing research, some cardiologists are concerned that some patients who initially respond well to cardiac resynchronization may later respond poorly.

SUMMARY

In general, the invention relates to techniques for providing adjustable cardiac resynchronization with an implanted medical device such as a pacemaker. Cardiac resynchronization may be adjusted, for example, by providing cardiac resynchronization during some time periods but not during other time periods. Cardiac resynchronization may also be adjusted by providing cardiac resynchronization in response to selected sensed events, rather than in response to all sensed events. Cardiac resynchronization may be further adjusted in both dimensions, by providing cardiac resynchronization at selected times and in response to selected sensed events.

An implanted medical device in accordance with the invention receives one or more programmed parameters pertaining to cardiac resynchronization. One parameter may be a ratio that defines which sensed events trigger cardiac resynchronization and which events do not. The ratio may be expressed, for example, as a number of synchronized paces to sensed events. In the bi-ventricular pacing context, the ratio may represent the number of bi-ventricular paces with respect to atrial senses. Time periods may also be programmed parameters. Cardiac resynchronization may be provided at programmed times, rather than throughout the day.

The programmed parameters may change. As the heart becomes more accustomed to cardiac resynchronization, more cardiac resynchronization may be provided. The implanted medical device may provide cardiac resynchronization according to a higher ratio of synchronized paces to sensed events, or for longer periods of time, or both.

In one embodiment, the invention is directed to a method comprising providing cardiac resynchronization to a heart during a first time period and refraining from providing cardiac resynchronization to the heart during a second time period. In one exemplary implementation, cardiac resynchronization is provided for a fraction of a day but not for the entire day. The method may further comprise changing the amount of cardiac resynchronization provided during the first time period. Although cardiac resynchronization is not provided during the second time period, other cardiac therapy may be provided during the second time period.

In another embodiment, the invention is directed to a method comprising providing cardiac resynchronization to a heart in response to a first sensed event and refraining from providing cardiac resynchronization to the heart in response to a second sensed event. In one exemplary implementation, cardiac resynchronization is provided according to a ratio of X:Y, in which cardiac resynchronization is performed X times for every Y sensed cardiac events. The method may further comprise changing the ratio. Although cardiac resynchronization is not provided in response to the second sensed event, other cardiac therapy may be provided in response to the second sensed event.

In an additional embodiment, the invention is directed to a method comprising sensing an atrial event, determining whether a bi-ventricular pace is indicated and delivering a bi-ventricular pace after the atrial event when the bi-ventricular pace is indicated. The method may also include receiving a ratio of X:Y, and indicating the bi-ventricular pace X times for every Y sensed atrial events. The method may also include receiving a time period, and indicating the bi-ventricular pace for atrial events occurring in the time period.

The invention may also be embodied as a computer-readable medium containing instructions that cause a programmable processor to carry out the above methods.

In a further embodiment, the invention is directed to a device comprising a first pacing electrode disposed proximal to a first chamber of a heart and a second pacing electrode disposed proximal to a second chamber of the heart. The device also includes an implanted medical device that determines whether cardiac resynchronization is indicated and delivers pacing pulses to the first and second pacing electrodes when cardiac resynchronization is indicated.

There are many advantages to adjustable cardiac resynchronization in accordance with the invention. Adjustable cardiac resynchronization includes the flexibility to pace less often than a device that provides cardiac resynchronization all of the time. Reduced pacing may result in a reduced workload on the heart, with a reduced risk of cardiac failure. Reduced pacing also conserves battery power.

Adjustable cardiac resynchronization may be used to train the patient's heart. Instead of receiving cardiac resynchronization all the time, the heart may receive dosages of cardiac resynchronization at particular times. In this way, the heart may become more acclimated to the therapy, and the associated increase in cardiac workload.

In addition, adjustable cardiac resynchronization accommodates other single-chamber or multiple-chamber pacing therapies. When the implanted medical device is not providing bi-ventricular pacing, for example, the device may be pacing a single ventricle.

The details of one or more embodiments of the invention are set forth in the accompanying drawings and the description below. Other features, objects, and advantages of the invention will be apparent from the description and drawings, and from the claims.

DETAILED DESCRIPTION

The techniques described below will be presented in the context of cardiac resynchronization to treat ventricular dysynchrony. The invention is not limited, however, to resynchronization of ventricular contractions. The invention may be implemented, for example, to resynchronize atrial contractions.

Figure 1:
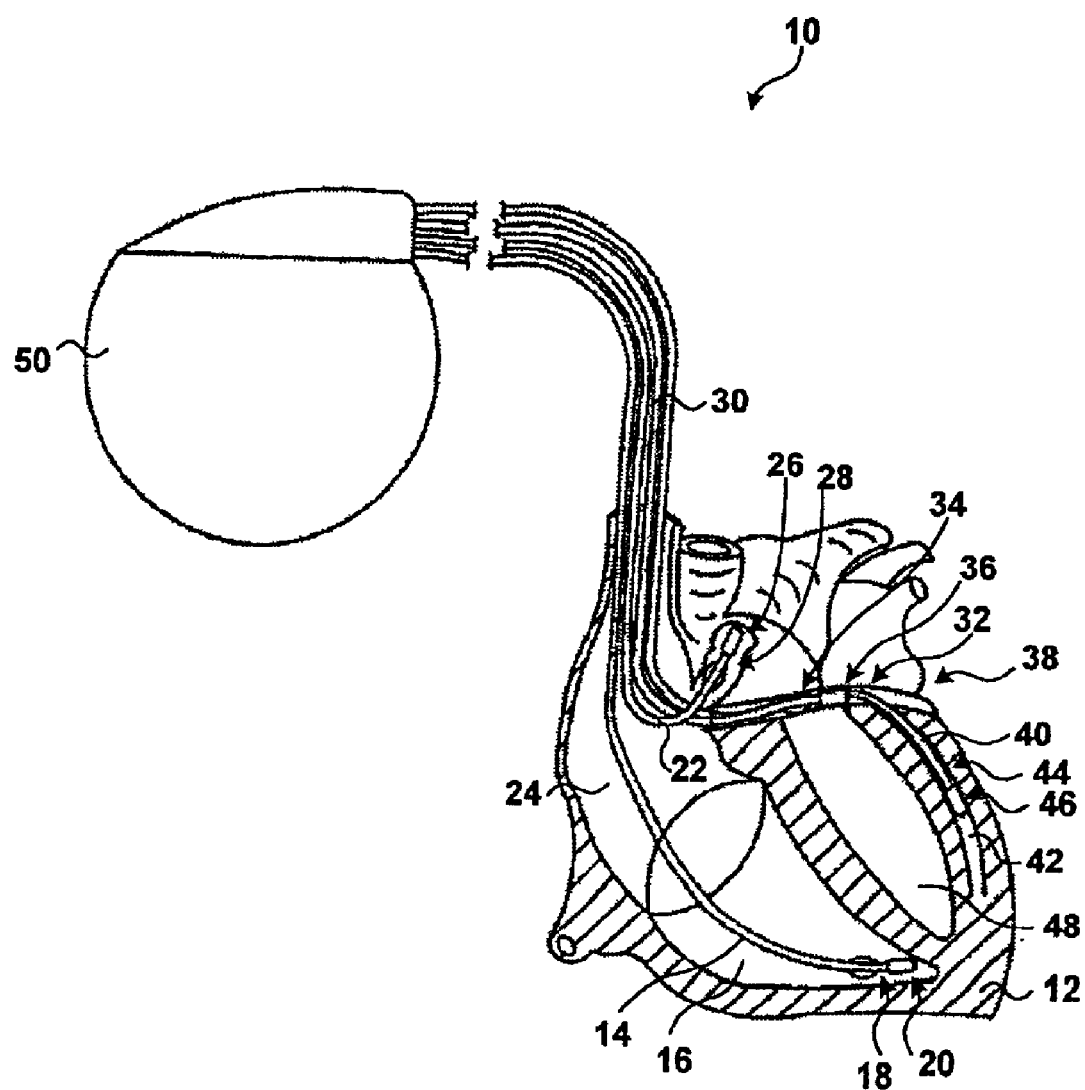
FIG. 1 is a diagram depicting an implanted medical device in which the invention may be practiced, in conjunction with a human heart.

FIG. 1 is a diagram illustrating an implanted medical device 10 in which the invention may be practiced. Implanted medical device 10, which is shown in conjunction with a human heart 12, comprises a four-chamber pacing system. Right ventricular pacing lead 14 is positioned conventionally in the right ventricle 16 such that its distal end is in the right ventricular apex of heart 12. Right ventricular pacing lead 14 carries bipolar electrodes 18 and 20 that sense electrical signals and can deliver pacing pulses to right ventricle 16.

Right atrial lead 22 is positioned so that its distal end is positioned within the right atrium 24. Right atrial lead 22 carries bipolar electrodes 26 and 28. Electrodes 26 and 28 sense electrical activity in right atrium 24 and may also deliver pacing pulses to right atrium 24.

Left atrial lead 30 is passed through right atrium 24 so that the distal end of lead 30 is positioned in the coronary sinus 32. Electrodes 34 and 36 on left atrial lead 30 sense electrical activity in the left atrium 38 and may also deliver pacing pulses to left atrium 38.

Left ventricular lead 40 is positioned via coronary sinus 32 in a cardiac vein 42, such as the middle or great cardiac vein. Distal electrodes 44 and 46 on left ventricular lead 40 are positioned for pacing and sensing with respect to the left ventricle 48.

Leads 14, 22, 30 and 40 are connected to a pacemaker 50 in a conventional manner. Pacemaker 50 receives electrical signals sensed by electrodes in the atria and ventricles, and may deliver pacing pulses to the atria and ventricles. In particular, pacemaker 50 receives an atrial sense from electrodes 26 or 28, and following a predetermined AV delay, delivers a bi-ventricular pace. Pacemaker 50 delivers a bi-ventricular pace by pacing right ventricle 16 and left ventricle 48 to cause cardiac resynchronization. The ventricles may be paced simultaneously, or one ventricle may be paced before the other. As will be described in more detail below, pacemaker 50 does not deliver bi-ventricular pacing after every atrial sense. Rather, pacemaker 50 adjusts cardiac resynchronization to acclimate the patient to the therapy.

Implanted medical device 10 is an exemplary device that may use the techniques of the invention. The invention is not limited to the device shown. For example, the invention may be practiced with unipolar electrodes rather than bipolar electrodes. The invention may further be practiced in a less complicated device, such as a device with two ventricular leads with sensing/pacing electrodes and a single atrial lead with a sensing electrode. Conversely, the invention may be practiced in a more complicated device as well, such as a device with each of the leads having more electrodes than are shown in FIG. 1.

Figure 2:
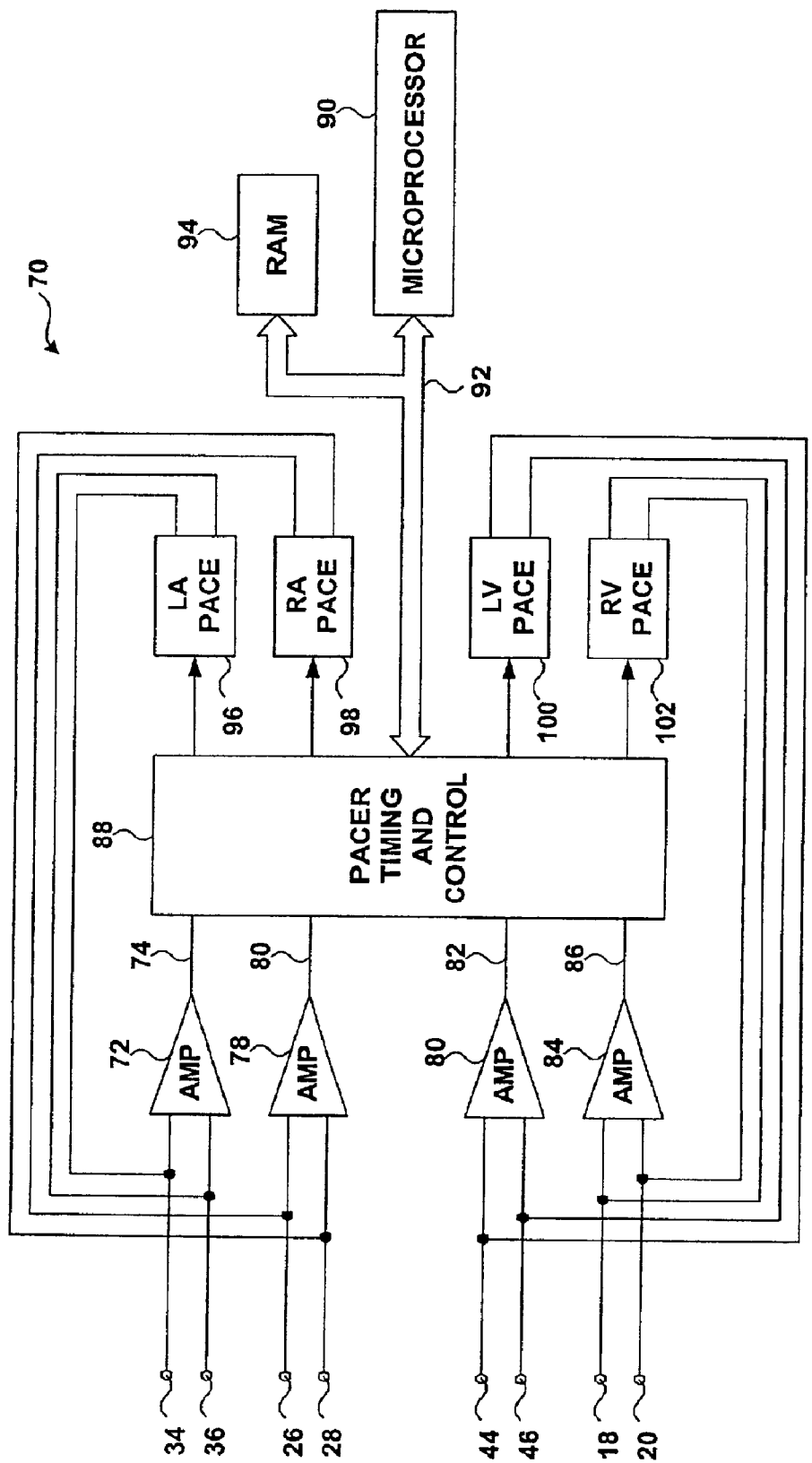
FIG. 2 is a block diagram of a multiple-chamber pacing system that implements the invention.

FIG. 2 is a block diagram of a system 70 that implements the invention. FIG. 2 is exemplary of the type of device in which the invention may be practiced, but the invention may be practiced in a wide variety of device implementations.

Electrodes 34 and 36 are located proximal to left atrium 38 and are coupled to a P-wave amplifier 72 in pacemaker 50. P-wave amplifier 72 may take the form of an automatic gain controlled amplifier providing an adjustable sensing threshold as a function of the amplitude of the P-wave sensed by electrodes 34 and 36. Amplifier 72 generates a signal on P-out line 74 whenever the signal sensed between electrodes 34 and 36 exceeds the sensing threshold. In like fashion, electrodes 26 and 28 are located proximal to right atrium 24 and are coupled to a P-wave amplifier 76. Amplifier 76 generates a signal on P-out line 78 whenever the signal sensed between electrodes 26 and 28 exceeds the sensing threshold.

Similarly, electrodes 44 and 46, located proximal to left ventricle 48, are coupled to an R-wave amplifier 80, and electrodes 18 and 20, located proximal to right ventricle 16, are coupled to another R-wave amplifier 84. Amplifier 80 generates a signal on R-out line 82 whenever the signal sensed between electrodes 44 and 46 exceeds the sensing threshold, and amplifier 84 generates a signal on R-out line 86 whenever the signal sensed between electrodes 18 and 20 exceeds the sensing threshold.

Pacer timing and control circuitry 88 receives the signals from P-out lines 74, 78 and R-out lines 82, 86. Pacer timing and control circuitry 88 preferably includes programmable digital counters that control the basic time intervals associated with modes of single-chamber pacing and multiple-chamber pacing.

Microprocessor 90 regulates pacer timing and control circuitry 88 by, for example, determining the appropriate pacing therapy and determining the amplitude of the cardiac pacing pulses. Microprocessor 90 loads pacing instructions to pacer timing and control circuitry 88 via bus 92. As will be described in more detail below, the instructions may include parameters pertaining to cardiac resynchronization ratios and/or cardiac resynchronization time parameters. These parameters may be programmed by the patient's physician and stored in memory such as random access memory (RAM) 94. The physician may, for example, program the parameters with a programmer, which communicates with implanted medical device 10 via telemetry.

When cardiac resynchronization or other pacing is indicated, pacer timing and control circuitry 88 triggers one or more pace pulse generators 96, 98, 100, 102. Pace pulses are transmitted from pace pulse generators 96, 98, 100, 102 to cardiac tissue via the corresponding electrodes. For example, a pacing pulse generated by right ventricle pace pulse generator 102 is delivered to right ventricle 16 via electrodes 18 and 20. In a bi-ventricular pace, pacer timing and control circuitry 88 triggers pacing pulses delivered from pace pulse generators 100 and 102.

The invention is not limited to the system 70 shown in FIG. 2. For example, the invention may be practiced in a pacemaker that provides defibrillation or cardioversion therapies. The invention may also be practiced, for example, in a system that provides for atrial sensing but not for atrial pacing, or in a system that includes no electrodes to sense or pace left atrium 38.

Moreover, microprocessor 90 and pacer timing and control circuitry 88 are depicted in FIG. 2 as logically distinct components, but the invention is not limited to such an arrangement. The invention may be implemented in a pacemaker that combines the functions of microprocessor 90 and pacer timing and control circuitry 88 in a single component. In particular, in some embodiments, the functions of pacer timing and control circuitry 88 may be programmed features of microprocessor 90. In the following described exemplary embodiments, determinations concerning cardiac resynchronization will be made by microprocessor 90, but such determinations may be made by another component such as pacer timing and control circuitry 88 or another processor not shown in FIG. 2.

Microprocessor 90 may be programmed to provide cardiac resynchronization in some situations but not in others. For example, microprocessor 90 may providing cardiac resynchronization to a heart in response to one sensed event, but may refrain from providing cardiac resynchronization to the heart in response to another sensed event. A ratio, received by microprocessor 90 as a programmed parameter, may define which sensed events result in cardiac resynchronization and which events do not.

The ratio may be expressed as a number of synchronized paces to a number of sensed events. In the context of bi-ventricular pacing, the ratio may represent the number of bi-ventricular paces with respect to atrial senses. For example, the ratio 1:4 indicates that one bi-ventricular pace will be provided for every four atrial senses, and the ratio 2:3 indicates that two bi-ventricular paces will be provided for every three atrial senses.

Any ratios may be employed, but the number of synchronized paces is generally less than or equal to the number of sensed events. When the number of synchronized paces is less than the number of sensed events, the patient receives cardiac resynchronization therapy following some sensed events, but not following every sensed event. Thus, cardiac resynchronization can be performed on a limited, "part-time" basis.

Figure 3:
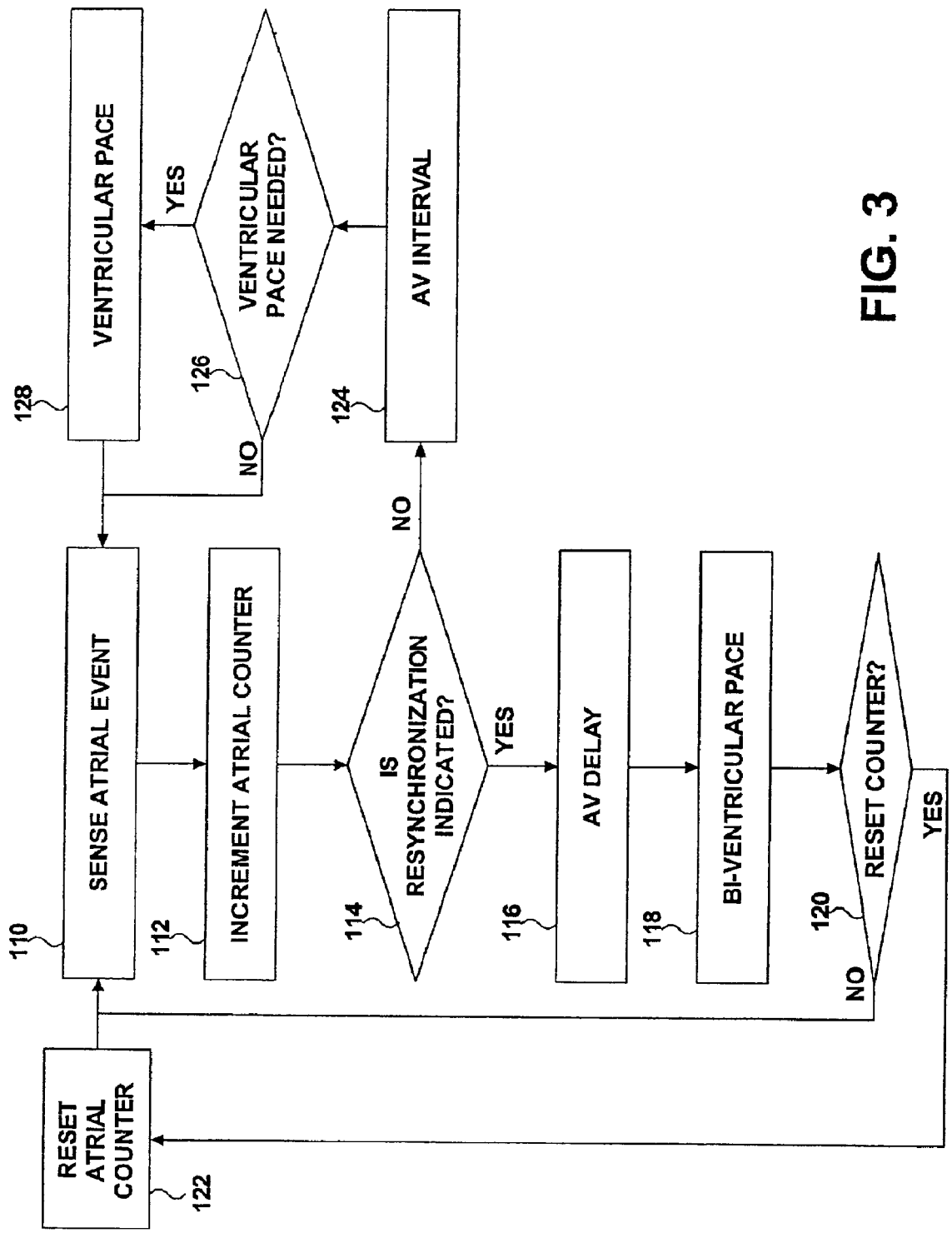
FIG. 3 is a flow diagram illustrating an exemplary operation of a technique for adjustable cardiac resynchronization.

FIG. 3 is a flow diagram illustrating an example operation of adjustable cardiac resynchronization using a synchronized-paces-to-sensed-events ratio in a bi-ventricular pacing context. It is assumed that microprocessor 90 has been programmed with a ratio. When atrial signals cause amplifier 76 to generate a signal on P-out line 78, for example, an atrial event is sensed (110). An atrial event results in incrementing an atrial event counter (112). The value of the atrial event counter affects whether cardiac resynchronization should be provided (114). In one exemplary implementation, when microprocessor 90 has been programmed with a 3:4 ratio, cardiac resynchronization is not indicated when the atrial counter equals 1, but cardiac resynchronization is indicated when the atrial counter equals 2, 3 or 4.

When cardiac resynchronization is indicated, there is a delay between the sensed atrial event and the provision of the bi-ventricular pace. This AV delay (116) corresponds to the time between atrial and bi-ventricular contractions. The AV delay may be shorter than the heart's natural AV delay, so that bi-ventricular pacing (118) will occur before the ventricles begin to contract autonomously.

The atrial counter may be reset (120, 122) at any time. In FIG. 3, microprocessor 90 resets the atrial counter as needed (120, 122) following bi-ventricular pacing (118).

The programmed ratio may be 1:1, meaning that bi-ventricular pacing follows every atrial sense. When the ratio is other than 1:1, however, there will be some atrial events that are not followed by bi-ventricular pacing. Even if bi-ventricular pacing does not occur, however, microprocessor 90 may be programmed to provide single-chamber pacing. FIG. 3 shows an exemplary relationship between bi-ventricular pacing and single-chamber pacing, and illustrated that cardiac resynchronization is not necessarily exclusive of other pacing strategies.

When cardiac resynchronization is not indicated (114), there is a delay between the sensed atrial event and the ventricular contraction. The ventricular contraction may be caused by a ventricular pace (128) or by the ventricle contracting on its own accord. In a typical implementation, pacing is postponed for an AV interval (124). When the ventricle contracts on its own accord during the AV interval, ventricular pacing is not needed (126). When the interval ends without ventricular activity, however, a ventricular pace is needed (126) and is delivered (128).

Figure 4:
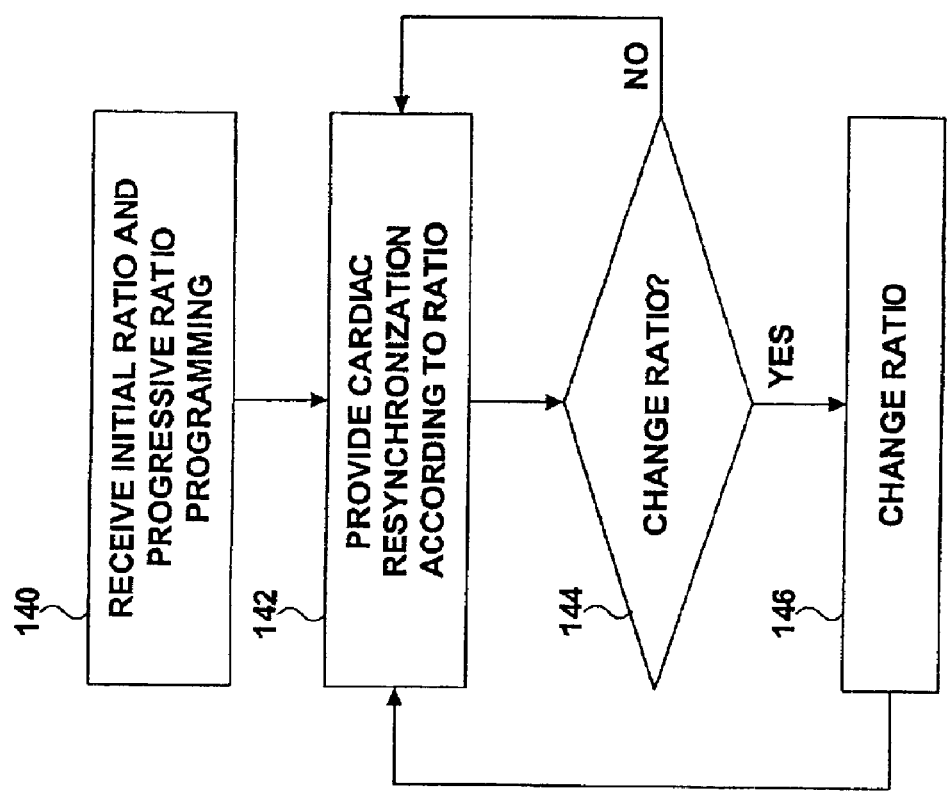
FIG. 4 is a flow diagram illustrating delivery of cardiac resynchronization with an adjustable ratio.

FIG. 4 is a flow diagram illustrating an embodiment of the invention. The programmed ratio of synchronized paces to sensed events need not be constant. A patient who is receiving cardiac resynchronization for the first time, for example, may not fully benefit from a 1:1 ratio, which may overwork the heart. Indeed, overwork could be problematic for some patients. Accordingly, a smaller ratio may be programmed initially, and the ratio may change as the patient becomes more acclimated to cardiac resynchronization.

Microprocessor 90 may be initially programmed with a small ratio such as 1:4 (140). Microprocessor 90 may further be programmed to change the ratio (140) to a higher ratio, such as 1:3, after a period of time. In some cases, microprocessor 90 may be programmed to progress the ratio in several stages, such as 1:4, followed by 1:3, followed by 1:2, followed by 2:3, followed by 3:4, followed by 1:1. At each stage, which may be progressed over the course of several months, the heart receives more cardiac resynchronization and becomes more trained to accept cardiac resynchronization therapy.

Microprocessor 90 provides cardiac resynchronization therapy according to the current ratio (142). Periodically, microprocessor 90 determines whether or not to change to a new ratio (144). This determination may be based upon passages of time, the past response of the patient to cardiac resynchronization, or other factors. When microprocessor 90 changes the ratio, microprocessor 90 provides cardiac resynchronization therapy according to the new ratio (146).

Figure 5:
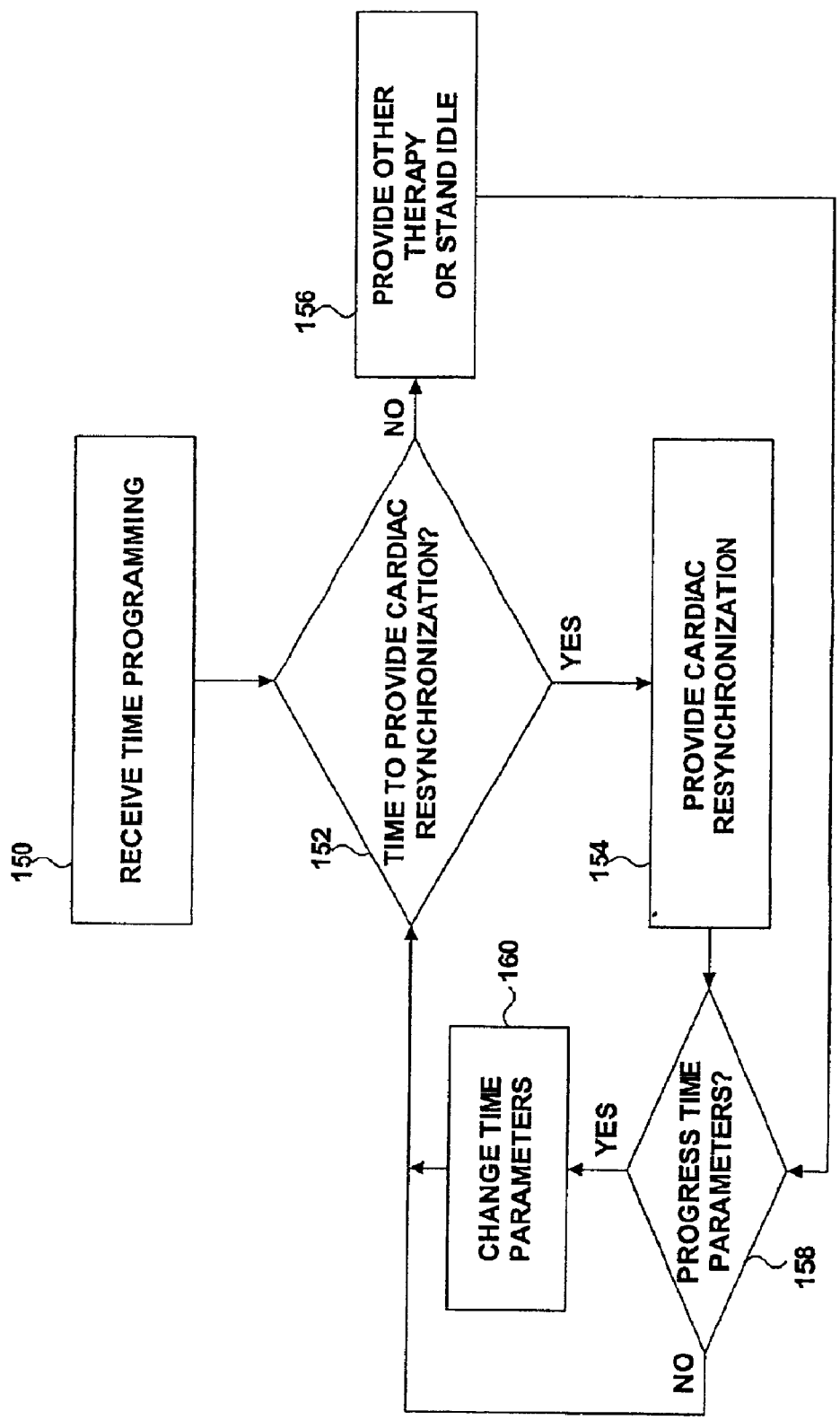
FIG. 5 is a flow diagram illustrating delivery of cardiac resynchronization with adjustable time parameters.

FIG. 5 is a flow diagram illustrating another embodiment of the invention. Cardiac resynchronization need not be provided all day, but may be provided at programmed times. Microprocessor 90 may provide cardiac resynchronization during one time period and may refrain from providing cardiac resynchronization during another time period.

For example, a patient who is receiving cardiac resynchronization for the first time may not fully benefit from cardiac resynchronization provided twenty-four hours go a day. The patient may derive more benefit if cardiac resynchronization is provided for only part of the day. The time periods for providing cardiac resynchronization therapy may progress in stages. The patient might receive two hours of cardiac resynchronization therapy per day during the first week, for example, four hours of cardiac resynchronization therapy per day during the following week, and six hours of cardiac resynchronization therapy per day during the week after that. This technique trains the heart to accept cardiac resynchronization therapy.

In addition, the patient may derive benefits from having cardiac resynchronization when needed. During the day, for example, the patient may be more active and may need the hemodynamic benefit of cardiac resynchronization. At night, however, the patient is less active and has less need for the hemodynamic benefit. Microprocessor 90 may refrain from providing cardiac resynchronization therapy during a time period when the therapy will be less beneficial.

Microprocessor 90 may be programmed with time parameters, i.e., instructions concerning the times when cardiac resynchronization is to be provided (150). For example, the parameters may include a duration of cardiac resynchronization therapy and the time or times of day that the therapy begins. The programming may further include instructions to change the parameters at a later reference time. For example, the patient may be provided one time period of therapy beginning at the outset of the first week, but the patient may be provided a longer time period of therapy beginning at the outset of the second week.

When it is time to provide cardiac resynchronization (152), microprocessor 90 provides the therapy (154). At other times, cardiac resynchronization is not indicated. Microprocessor 90 may nevertheless provide other therapy (156), such as single-chamber pacing, or may provide no additional therapy. Microprocessor 90 further changes the time parameters when needed (158, 160).

The embodiments shown in FIGS. 4 and 5 are not exclusive other pacing therapies. Furthermore, the embodiments of FIGS. 4 and 5 are not exclusive of each other, but rather may be combined with one another. Microprocessor 90 may be programmed, for example, to provide cardiac resynchronization therapy for two hours every morning in a 1:4 ratio. Moreover, the adjustable cardiac resynchronization techniques demonstrated in FIGS. 4 and 5 are not limited to bi-ventricular pacing. Programmed ratios and times may also be beneficial with, for example, bi-atrial pacing.

Figure 6:
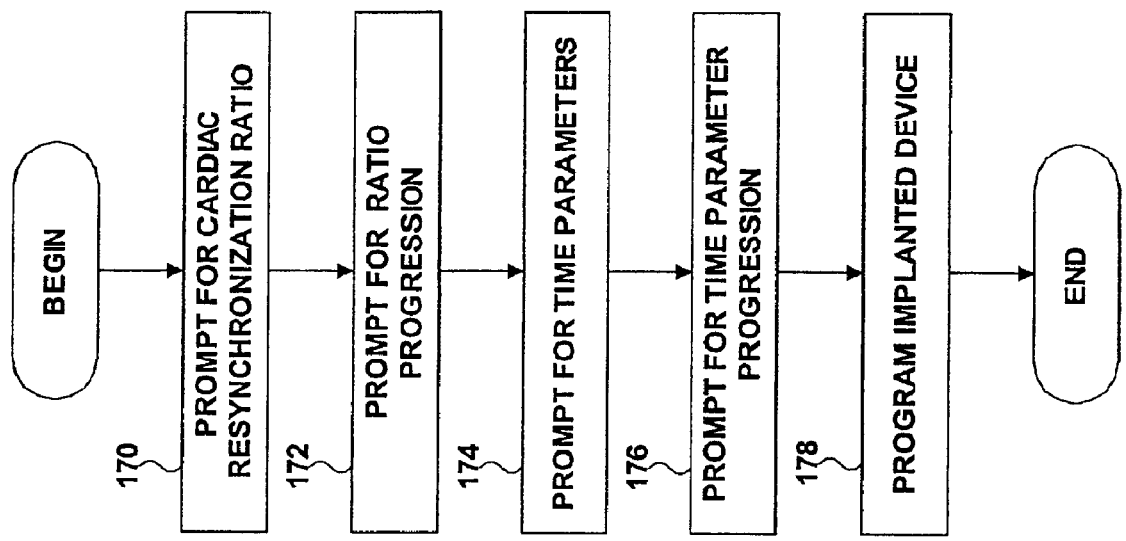
FIG. 6 is a flow diagram illustrating programming of an implanted medical device to deliver cardiac resynchronization.

FIG. 6 is a flow diagram illustrating a further embodiment of the invention. As described above, ratio and/or time parameters may be programmed by the patient's physician. FIG. 6 illustrates a technique for programming the parameters. The techniques may be applied by implanted medical device 10 or by an intermediate device, such as a programmer, that programs implanted medical device 10 with the parameters. In the following described exemplary embodiment, the techniques will carried out by a programmer, but such techniques are not limited to use with a programmer.

When cardiac resynchronization is to be a part of the therapy for the patient, the programmer prompts the physician for a cardiac resynchronization ratio (170). The physician elects to provide a ratio or not to provide a ratio. When the physician provides a ratio, the programmer prompts the physician for instructions regarding progression of the ratio (172). For example, the physician may initially program a 1:4 ratio, and may specify that the ratio change to 1:3 after ten days. The physician may program several stages of progression.

The programmer prompts the physician for time parameters (174), which the physician elects to provide or not to provide. When the physician provides time parameters, the programmer prompts the physician for instructions regarding progression of the time parameters (176). For example, the physician may initially program cardiac resynchronization therapy for two hours once a day, and may specify that the therapy shall increase to two hours twice a day after ten days.

The programmer programs implanted medical device 10 (178). The programmer may perform additional steps not shown in FIG. 6. For example, the programmer may confirm the physician's instructions and/or point out any inconsistencies in the instructions.

There are many advantages to adjustable cardiac resynchronization. Adjustable cardiac resynchronization includes the flexibility to pace less often than a device that provides cardiac resynchronization all the time. Reduced pacing may result in a reduced workload on the heart, with a reduced risk of cardiac failure. Reduced pacing also conserves battery power.

Adjustable cardiac resynchronization may be used to train the patient's heart. Instead of receiving cardiac resynchronization all the time, the heart may receive dosages of cardiac resynchronization at particular times. In this way, the heart may become more acclimated to the therapy.

In addition, adjustable cardiac resynchronization accommodates other single-chamber or multiple-chamber pacing therapies. When the implanted medical device is not providing bi-ventricular pacing, for example, the device may be pacing a single ventricle.

Various embodiments of the invention have been described. The techniques described above may be embodied in a computer-readable medium containing instructions. The instructions may cause a programmable processor such as microprocessor 90 to implement the techniques. These and other embodiments are within the scope of the following claims.

What is claimed is:

1. A method comprising:
   providing cardiac resynchronization to a heart in response to a first sensed event; and
   refraining from providing cardiac resynchronization to the heart in response to a second sensed event further comprising:

receiving a ratio of X:Y; and performing cardiac resynchronization X times for every Y sensed cardiac events.

2. The method of claim 1, further comprising:

receiving a second ratio of X2:Y2; and performing cardiac resynchronization X2 times for every Y2 sensed cardiac events.

3. A method comprising:

sensing an atrial event;

determining whether a bi-ventricular pace is indicated; and delivering a bi-ventricular pace after the atrial event when the bi-ventricular pace is indicated and further comprising receiving a ratio of X:Y, wherein the bi-ventricular pace is indicated X times for every Y sensed atrial events.

4. A method comprising:

sensing an atrial event;

determining whether a bi-ventricular pace is indicated; and delivering a bi-ventricular pace after the atrial event when the bi-ventricular pace is indicated and further comprising receiving a time period, wherein the bi-ventricular pace is indicated for atrial events occurring in the time period.

5. A method comprising:

receiving a ratio of X:Y;

sensing a cardiac event; and applying a synchronized cardiac pace in response to the cardiac event, wherein X represents a number of synchronized cardiac paces, wherein Y represents a number of sensed cardiac events, and wherein X is less than Y.

6. The method of claim 5, further comprising performing cardiac resynchronization X times for every Y sensed cardiac events, wherein performing cardiac resynchronization comprises:

delivering a first pace to a first chamber of a heart; and delivering a second pace to a second chamber of the heart synchronized with the first pace.

7. The method of claim 5, further comprising receiving a second ratio of X2:Y2, wherein the second ratio X2;Y2 is different from the ratio X:Y; and performing cardiac resynchronization X2 times for every Y2 sensed cardiac events, wherein performing cardiac resynchronization comprises:

delivering a first pace to a first chamber of a heart; and delivering a second pace to a second chamber of the heart synchronized with the first pace.

8. The method of claim 5, wherein sensing a cardiac event comprises sensing an atrial event.

9. The method of claim 5, wherein synchronized cardiac paces comprises bi-ventricular paces.

10. A device comprising:

a pacing circuit that applies cardiac resynchronization to a heart; and a processor that controls the pacing circuit to apply the cardiac resynchronization during a first period and refrain from applying the cardiac resynchronization during a second time period and further comprising memory that stores the duration of the first period.

11. A device comprising:

a pacing circuit that applies a synchronized cardiac pace to a heart;

a processor that senses a cardiac event and controls the pacing circuit to apply the synchronized cardiac pace in response to the cardiac event; and memory that stores a ratio X:Y, wherein X represents a number of synchronized cardiac paces, wherein Y represents a number of sensed cardiac events, and wherein X is less than Y.

12. The device of claim 11, wherein the processor controls the pacing circuit to apply the synchronized cardiac pace X times for every Y cardiac events.

13. The device of claim 11, further comprising:

a first pacing electrode disposed proximal to a first chamber of a heart; and a second pacing electrode disposed proximal to a second chamber of the heart;

wherein the processor controls the pacing circuit to apply the synchronized cardiac pace via the first pacing electrode and the second pacing electrode.

14. The device of claim 11, further comprising a sensing electrode disposed proximal to the heart, wherein the processor senses the cardiac event via the sensing electrode.

15. A computer-readable medium containing instructions, the instructions causing a programmable processor to:

provide cardiac resynchronization to a heart in response to a first sensed event; and refrain from providing cardiac resynchronization to the heart in response to a second sensed event wherein the instructions further causing a programmable processor to:

receive a ratio of X:Y; and perform cardiac resynchronization X times for every Y sensed cardiac events.

16. The medium of claim 15, the instructions further causing a programmable processor to:

receive a second ratio of X2:Y2; and perform cardiac resynchronization X2 times for every Y2 sensed cardiac events.

* * * * *

UNITED STATES PATENT AND TRADEMARK OFFICE
CERTIFICATE OF CORRECTION

PATENT NO. : 6,842,642 B2
DATED : January 11, 2005
INVENTOR(S) : Warren L. Vanhout It is certified that error appears in the above-identified patent and that said Letters Patent is hereby corrected as shown below:

Column 9,
Line 48, delete "ratio X2; Y2" and insert -- ratio X2: Y2 --.

Signed and Sealed this

Twenty-fourth Day of May, 2005

JON W. DUDAS
*Director of the United States Patent and Trademark Office*